(12) United States Patent
Donnelly

(10) Patent No.: US 12,409,294 B2
(45) Date of Patent: *Sep. 9, 2025

(54) FLOAT RETENTION ARRANGEMENT FOR HUMIDIFICATION CHAMBER

(71) Applicant: Fisher & Paykel Healthcare Limited, Auckland (NZ)

(72) Inventor: Jess Edward Donnelly, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,446

(22) Filed: Aug. 30, 2023

(65) Prior Publication Data

US 2023/0414897 A1 Dec. 28, 2023

Related U.S. Application Data

(63) Continuation of application No. 17/303,588, filed on Jun. 2, 2021, now Pat. No. 11,786,692, which is a continuation of application No. 16/255,175, filed on Jan. 23, 2019, now Pat. No. 11,052,218, which is a continuation of application No. 14/914,510, filed as application No. PCT/NZ2014/000177 on Aug. 26, 2014, now Pat. No. 10,207,074.

(Continued)

(51) Int. Cl.
*A61M 16/16* (2006.01)
*A61M 16/08* (2006.01)
*F16K 31/26* (2006.01)

(52) U.S. Cl.
CPC ...... *A61M 16/168* (2014.02); *A61M 16/0816* (2013.01); *A61M 16/167* (2014.02); *F16K 31/26* (2013.01)

(58) Field of Classification Search
CPC . A61M 16/165; A61M 16/167; A61M 16/168
See application file for complete search history.

(56) References Cited

U.S. PATENT DOCUMENTS

| 2,989,053 | A | 6/1961 | Hamilton |
| 3,316,908 | A | 5/1967 | Burke |

(Continued)

FOREIGN PATENT DOCUMENTS

WO     WO 2013/162386     10/2013

OTHER PUBLICATIONS

PCT Application No. PCT/NZ2014/000177 International Search Report and Written Opinion Mailed Nov. 17, 2014, in 8 pages.

*Primary Examiner* — Kathryn E Ditmer
(74) *Attorney, Agent, or Firm* — VIA LLP

(57) ABSTRACT

A float retention arrangement and related methods for a humidification chamber that includes at least one float that operates an inlet valve that controls a flow of water through a water inlet opening of the humidification chamber. A cover of the humidification chamber defines an interior space, at least one gas port and a float retention opening. A component forms at least a portion of a water supply conduit for supplying water from a water source to the water inlet opening. The component is insertable into the float retention opening and is positionable to contact and retain the at least one float in a non-use position. In some configurations, the component can be a water spike.

20 Claims, 7 Drawing Sheets

Related U.S. Application Data

(60) Provisional application No. 61/873,777, filed on Sep. 4, 2013.

(56) References Cited

U.S. PATENT DOCUMENTS

| | | | |
|---|---|---|---|
| 3,822,700 A | 7/1974 | Pennington | |
| 4,045,525 A | 8/1977 | Huggins | |
| 4,173,223 A | 11/1979 | Raines et al. | |
| D257,886 S | 1/1981 | Kersten | |
| 4,262,671 A | 4/1981 | Kersten | |
| D267,270 S | 12/1982 | Mittleman | |
| 4,405,315 A | 9/1983 | Handt | |
| 4,411,661 A | 10/1983 | Kersten | |
| D272,850 S | 2/1984 | Kulle | |
| 4,573,967 A | 3/1986 | Hargrove et al. | |
| 4,665,391 A | 5/1987 | Spani | |
| 4,834,744 A | 5/1989 | Ritson | |
| 4,926,856 A * | 5/1990 | Cambio, Jr. | A61M 16/164 604/407 |
| 5,071,413 A | 12/1991 | Utterberg | |
| 5,098,407 A | 3/1992 | Okamura | |
| 5,125,911 A | 6/1992 | Grabenkort et al. | |
| 5,195,515 A | 3/1993 | Levine | |
| 5,267,412 A | 12/1993 | Bergin | |
| 5,400,923 A | 3/1995 | Golias et al. | |
| 5,445,143 A * | 8/1995 | Sims | A61M 16/168 251/210 |
| 5,445,630 A | 8/1995 | Richmond | |
| 5,618,000 A | 4/1997 | Lantzy et al. | |
| 5,833,674 A * | 11/1998 | Turnbull | A61M 39/045 604/905 |
| 5,943,473 A | 8/1999 | Levine | |
| 6,183,453 B1 | 2/2001 | Swisher | |
| 6,261,267 B1 | 7/2001 | Chen | |
| 10,207,074 B2 | 2/2019 | Donnelly | |
| 11,052,218 B2 | 7/2021 | Donnelly | |
| 11,786,692 B2 | 10/2023 | Donnelly | |
| 2004/0050386 A1 * | 3/2004 | Levine | A61M 16/167 128/203.16 |
| 2004/0108393 A1 | 6/2004 | Thayer et al. | |
| 2005/0182383 A1 | 8/2005 | Wallen | |
| 2006/0081258 A1 | 4/2006 | Nalagatla et al. | |
| 2008/0054500 A1 | 3/2008 | Bradley et al. | |
| 2009/0005753 A1 | 1/2009 | Browne | |
| 2009/0254031 A1 | 10/2009 | Lee | |
| 2010/0170511 A1 * | 7/2010 | Payne | A61M 16/167 137/423 |
| 2011/0108028 A1 * | 5/2011 | Zollinger | A61M 16/168 128/203.12 |
| 2011/0156289 A1 * | 6/2011 | Steg | A61M 16/168 261/DIG. 65 |
| 2012/0203194 A1 | 8/2012 | Cederschiold et al. | |
| 2014/0150911 A1 | 6/2014 | Hanner et al. | |
| 2016/0228671 A1 | 8/2016 | Jackson et al. | |

\* cited by examiner

FLOAT RETENTION ARRANGEMENT FOR HUMIDIFICATION CHAMBER

INCORPORATION BY REFERENCE

The present application is a continuation application of U.S. patent application Ser. No. 17/303,588, filed Jun. 2, 2021, which is a continuation application of U.S. patent application Ser. No. 16/255,175, filed Jan. 23, 2019, now U.S. Pat. No. 11,052,218, which is a continuation application of U.S. patent application Ser. No. 14/914,510, filed Feb. 25, 2016, now U.S. Pat. No. 10,207,074, which is a national stage application under 35 U.S.C. § 371 (c) of PCT Application No. PCT/NZ2014/000177, filed Aug. 26, 2014, which is related to and claims priority to U.S. Provisional Patent Application No. 61/873,777, filed Sep. 4, 2013, the entireties of which are hereby incorporated by reference herein and made a part of the present disclosure.

BACKGROUND

Field

The present disclosure relates to humidifiers for respiratory support systems. More particularly, the present disclosure relates to a float retention arrangement for a humidification chamber.

Description of Related Art

In a humidification chamber, one or more floats regulate the level of water flowing into the chamber by controlling a fill valve. Float retention devices are used to hold the float(s) in a desired position post-manufacture to prevent or reduce occurrence of impact damage and fatigue to the components of the float valve mechanism during transport and storage. The float valve mechanism comprises floats, lift arms, valve diaphragms, and float hinges. Damage to any component of the float valve mechanism could result in an uncontrolled water level within the chamber, which is undesirable. Typically, the float retention device holds the float in a position corresponding to an open position of the water inlet valve.

Prior art float retention devices, or float retainers, are often assembled onto the gas inlet and outlet ports, typically during manufacture. The float retainer is intended to be removed and discarded by the user at the point-of-use. The float retainer can incorporate port caps, which can provide a substantially airtight seal to inhibit or prevent ingress of foreign material into the inlet or outlet ports during transport and storage.

As described above, typically, the water inlet valve is held open by the float retainer. Thus, the humidification chamber could overfill if the water spike, which provides water to the water inlet valve, is inserted into a water source before the float retainer is removed. In addition, the float retainer precludes factory pre-assembly of breathing tubes and adapters to the chamber because the float retainer obstructs the inlet and outlet ports until removed by the end user at the point-of-use.

SUMMARY

The systems, methods and devices described herein have innovative aspects, no single one of which is indispensable or solely responsible for their desirable attributes. Without limiting the scope of the claims, some of the advantageous features will now be summarized.

In some configurations, a humidification chamber comprises a cover defining an interior space. The cover comprises at least one gas port, a water inlet opening and a float retention opening. At least one float operates an inlet valve that controls a flow of water through the water inlet opening. A water supply conduit has a first end and a second end. The first end is connected to the water inlet opening. An adapter is connected to the second end of the water supply conduit and is configured, in use, to couple the water supply conduit to a source of water. The adapter is insertable into the float retention opening and is positionable to contact and retain the at least one float in a non-use position.

In some configurations, the adapter is a water spike.

In some configurations, the at least one float comprises a primary float and a secondary float.

In some configurations, the at least one gas port comprises a gas inlet port and a gas outlet port.

In some configurations, the water spike comprises a handle.

In some configurations, a tip of the water spike contacts the at least one float.

In some configurations, when the adapter is positioned in the float retention opening, the adapter does not obstruct the at least one gas port such that breathing tubes, adapters or other components can be coupled to the at least one gas port with the adapter positioned in the float retention opening.

In some configurations, a humidification chamber comprises a cover defining an interior space. The cover comprises at least one gas port, a water inlet opening and a float retention opening. At least one float operates an inlet valve that controls a flow of water through the water inlet opening. A component forms at least a portion of a water supply conduit for supplying water from a water source to the water inlet opening. The component is insertable into the float retention opening and is positionable to contact and retain the at least one float in a non-use position.

In some configurations, the at least one float comprises a primary float and a secondary float.

In some configurations, the at least one gas port comprises a gas inlet port and a gas outlet port.

In some configurations, a method of retaining a float of a humidification chamber comprises inserting an adapter that is connected to a free end of a water supply conduit through a float retention opening in a cover of the humidification chamber until the adapter moves and retains the float in a non-use position, wherein an end of the water supply conduit opposite the free end is coupled to a water inlet of the humidification chamber.

In some configurations, a method of using a humidification chamber comprises removing an adapter that is connected to a free end of a water supply conduit from a float retention opening in a cover of the humidification chamber to release a float from a non-use position, wherein an end of the water supply conduit opposite the free end is coupled to a water inlet of the humidification chamber.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
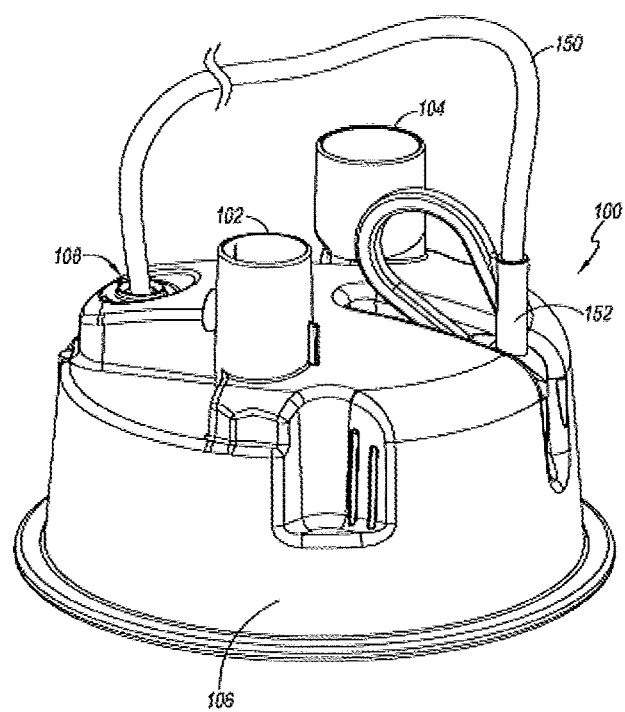
FIG. 1 is a perspective view of a humidification chamber having a float retention arrangement, which preferably comprises a water spike inserted into the chamber to retain the float(s) in a non-use (e.g., storage and/or shipping) position.
Figure 2:
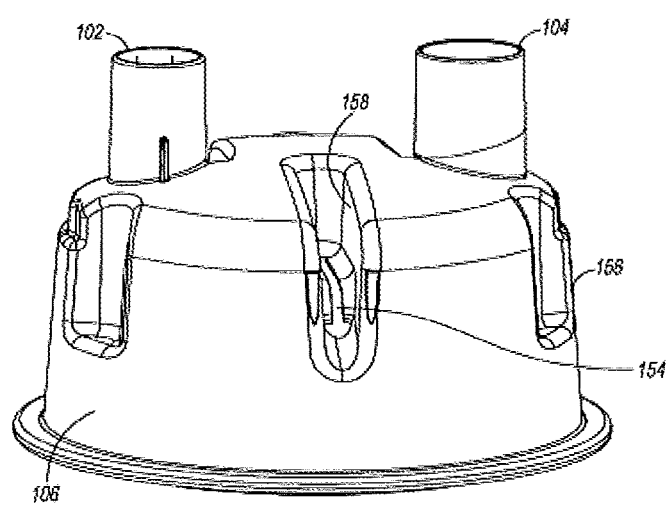
FIG. 2 is a front view of the humidification chamber of FIG. 1 with the water spike removed to illustrate an access opening through which the water spike can be inserted.
Figure 3:
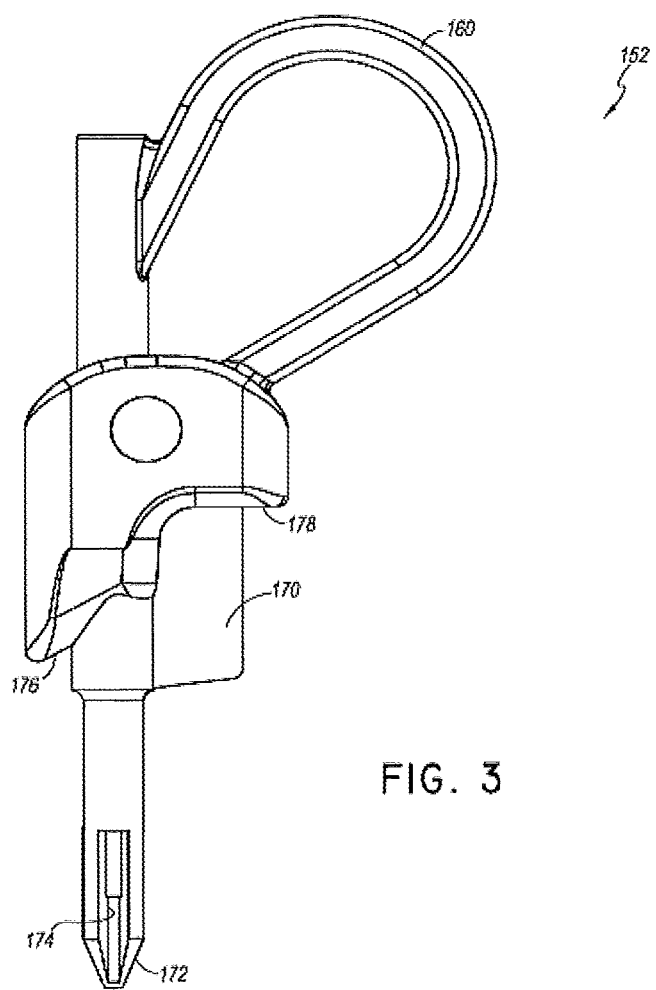
FIG. 3 is a side view of the water spike separate from the humidification chamber.

In one or more embodiments of the present humidification chamber, a component of the humidification chamber is utilized as a float retainer in at least one mode of the humidification chamber, such as a storage or shipping mode, for example and without limitation. The component preferably is a component that has utility in connection with the use of the humidification chamber other than use as a float retainer. For example, in some configurations, the component used as a float retainer is or includes an adapter for connecting the humidification chamber to a source of water (e.g., a water spike). In at least some configurations, the water spike can be inserted through an access opening in the chamber cover, wherein the access opening is separate from the gas inlet port and the gas outlet port. The access opening can be separate from the water inlet. The humidification chamber can be of any suitable arrangement that includes one or more floats (or other movable components) that are desirably held in a particular position (e.g., open or a non-use position) under certain circumstances (e.g., during non-use, such as shipping or storage). An example of a humidification chamber is described below. Components or features of the humidification chamber not discussed in detail herein can be of any suitable construction, such as the same as or similar to corresponding components or features of the humidification chambers disclosed in Applicant's PCT Publication No. WO2013/162386, entitled USABILITY FEATURES FOR RESPIRATORY HUMIDIFICATION SYSTEM, and related U.S. priority application Nos. 61/639,632 and 61/785,733, the entireties of which are hereby incorporated by reference herein. However, other suitable arrangements can also be used.

With reference to FIGS. 1-4, the humidification chamber 100 generally comprises a housing defining an internal space, an inlet port 102 and an outlet port 104, each of which communicate with the internal space of the humidification chamber 100. In use, gases flow into the humidification chamber 100 via the inlet port 102. The gases are humidified within the humidification chamber 100 and flow out of the humidification chamber 100 through the outlet port 104.

The humidification chamber 100 is configured to be installed on a heater plate of an associated humidifier, such that a base 106 of the humidification chamber 100 contacts the heater plate of the humidifier. The base 106 preferably comprises a metal with good thermal conductivity, such as aluminum or copper, for example and without limitation. The humidification chamber 100 is further configured to hold a volume of a liquid, such as water. In use, the liquid contacts the base 106. The base 106 is heated by the heater plate, which causes at least some of liquid in the humidification chamber 100 to evaporate.

A water reservoir, such as a water bag (not shown), supplies liquid water to the humidification chamber 100 through a water inlet 108 in use. As discussed, the humidification chamber 100 contains water in both liquid and vapor phases as a result of heat energy supplied through the heat transfer base 106 by the heater plate of the associated humidifier. Liquid water enters the humidification chamber 100 through the water inlet 108 and rises to a level dependent on the amount of water allowed to enter the humidification chamber 100 by a suitable control arrangement, such as one or more valves.

In the illustrated arrangement, a dual valve arrangement 110 controls the entry of liquid water from the water reservoir or other water supply into the humidification chamber 100. The illustrated dual valve arrangement 110 comprises a primary valve arrangement 112 ("primary valve 112") and a secondary valve arrangement 114 ("secondary valve 114"). At least one of the primary valve 112 and the secondary valve 114 is controlled by a float. In the illustrated arrangement, the primary valve 112 is controlled by a primary float 116, which can be at least partially constructed of an air or gas-filled, sealed or unsealed element or other buoyant structure which is able to rise and fall with the water level. In the illustrated arrangement, the primary float 116 includes a vent 116a that opens on an upper surface of the float 116 at a position above the normal water line. The vent 116a connects the interior of the primary float 116 with the air space within the humidification chamber 100 to avoid or reduce volume changes of the primary float 116 as a result of pressure or temperature changes within the humidification chamber 100.

Preferably, the secondary valve 114 is also controlled by a float, which is referred to herein as a secondary float 117. The secondary float 117 can be at least partially constructed of an air or gas-filled, sealed or unsealed element or other buoyant structure in a manner similar to the primary float 116. In the illustrated arrangement, the secondary float 117 does not include a vent. The larger volume compared to the primary float 116 and the secondary, back-up functionality of the secondary float 117 reduces or eliminates the advantages of a vent in the secondary float 117. That is, the secondary float 117 generally operates only in the event of a malfunction of the primary float 116 to shut off the supply of water to the humidification chamber 100. Thus, fine control of the secondary valve 117 is not necessarily required and changes in buoyancy due to volume changes can be tolerated. However, in some arrangements, a vent could be provided.

In some configurations, one of the valves 112, 114 is not controlled by a float, but is operated by an alternative arrangement. For example, the secondary valve 114 can be controlled by an alternative arrangement, such as a water level sensor and actuator arrangement, so that the usual secondary float can be omitted to provide additional useful volume within the humidification chamber 100 or space for other components or arrangements. In such configurations, the float retention arrangement can be modified accordingly from that illustrated herein.

The illustrated first or primary float 116 includes a coupling arrangement, such as a coupling arm 118, which is pivotally connected to support, such as a hinge bracket 120, for movement about an axis of rotation of the primary float 116. The hinge bracket 120 can be supported by any suitable portion of the humidification chamber body. For example, an upper portion of the hinge bracket 120 can be coupled (e.g., fastened, snap-fit or bonded) to the water inlet 108 portion of the humidification chamber body and, if desired, a lower portion of the hinge bracket 120 can rest against a side surface of the humidification chamber body. Thus, the primary float 116 rises and falls along with the water level within the humidification chamber 100.

The primary float 116 actuates the primary valve 112. In particular, the primary float 116 moves a push rod 124, which includes a first portion or lower end portion 128 pivotally coupled to the coupling arm 118 of the primary float 116 and a second portion or upper end portion 126. The upper end portion 126 includes a valve body 130 that cooperates with a first valve seat 132 of the dual valve arrangement 110. The valve body 130 and first valve seat 132 form a portion of the first or primary valve 112. The valve body 130 can engage the first valve seat 132, directly or indirectly, to close the primary valve 112 and create at least a substantial seal that inhibits or substantially prevents water from entering the humidification chamber 100 through the primary valve 112. The valve body 130 can also be disengaged from the first valve seat 132 to open the primary valve 112 and permit entry of water into the humidification chamber 100. The primary float 116, coupling arm 118, push rod 124 and first valve seat 132 are sized, proportioned, arranged or otherwise configured to close the primary valve 112 once a desirable water level within the humidification chamber 100 is reached and to open the primary valve 112 when the actual water level falls below the desirable water level thereby preferably maintaining the actual water level at or near the desirable water level.

The secondary valve 114 operates in conjunction with the primary valve 112 as a redundant or failsafe arrangement. Preferably, the primary valve 112 controls the entry of water into the humidification chamber 100 under normal operating conditions. However, if the primary valve 112 should malfunction or, for whatever reason, the water level should rise above the desirable water level, the secondary valve 114 preferably closes to inhibit or stop water from entering the humidification chamber 100. The secondary valve 114 can also open when the water level falls below the desirable water level to permit refill of water and continued use of the humidifier 107.

The secondary valve 114 includes a movable valve body assembly 134 that is movable between a closed position, in which a valve body element 136 directly or indirectly engages a second valve seat 138 of the secondary valve 114 to inhibit or stop water from entering the humidification chamber 100 through the secondary valve 114, and an open position, in which the valve body element 136 does not engage or close the second valve seat 138 of the secondary valve 114 so that water is permitted to enter the humidification chamber 100 through the secondary valve 114.

In the illustrated arrangement, the valve body assembly 134 is pivotally connected to the hinge bracket 120 for movement about an axis of rotation. The illustrated valve body assembly 134 includes a base 142 and a retainer cap 144 that support a push tube 146 therebetween. The base 142 is rotatably supported by the hinge bracket 120. The push tube 146 defines or carries the valve body element 136. Preferably, the base 142 defines a hemispherical portion and the push tube 146 defines a complementary hemispherical portion that cooperate to form a ball-joint arrangement, which permits rotation of the push tube 146 relative to the base 142 about two axes of rotation. Accordingly, a desirable orientation of the push tube 146 can be maintained throughout a range of pivotal movement of the base 142. In some configurations, the hemispherical portions can be cylindrical such that the base 142 and push tube 146 are movable about a single axis relative to one another. The retainer cap 144 can be secured to the base 142 by any suitable arrangement, such as a snap-fit arrangement, mechanical fasteners, adhesives or ultrasonic welding, for example and without limitation. Preferably, a space is provided between the retainer cap 144 and the push tube 146 such that the retainer cap 144 inhibits separation of the push tube 146 from the base 142, while allowing for relatively free movement of the push tube 146 relative to the base 142.

In the illustrated arrangement, the push rod 124 is co-axial with the push tube 146. The push rod 124 and push tube 146 are capable of moving freely and independently of one another. The end of the push rod 124 facing the water inlet 108 is tapered to a blunt point, which forms the valve body 130. The valve body 130 of the push rod 124 and the valve body element 136 of the push tube 146 can be covered by a valve seal element, which can be a flexible sealing membrane. Such a valve seal element can be configured to fit snugly over the rim of the push tube 146, thus coupling the push tube 146 to the push rod 124 in a floating connection. Thus, in such a configuration, the valve seal element can directly contact the first valve seat 132 and the second valve seat 138 when the respective valve is in a closed position. In addition, the valve seal element can prevent water from entering the humidification chamber 100 through the water inlet 108 when the secondary valve 114 is closed regardless of the position of the primary valve 112. The valve seal element can be made of material that is supple but strong, for example, a medical grade silicone rubber material.

As described above, water is supplied to the humidification chamber 100 from a water source by a supply tube arrangement comprising a supply tube 150. One end of the supply tube 150 is coupled to the water inlet 108 and the other end of the supply tube 150 is coupled to an adapter for coupling the supply tube 150 to a source of water. The adapter can be in the form of a water spike 152, for example. Preferably, the water spike 152 can also be used as a float retention device.

In at least some configurations, the water spike 152 can be inserted through an access opening 154 in the humidification chamber 100, such as in a chamber cover 156, for example. The access opening 154 can be in the form of a slot and, in at least some configurations, can be located within a recess 158 defined by the cover 156. The recess 158 positions the water spike 152 in close proximity with the floats 116, 117, so that the water spike 152 does not need to be excessively long in order to contact the floats 116, 117, while preserving the desired volume of the humidification chamber 100. Accordingly, in at least some configurations, one or more dimensions (e.g., a width) of the recess 158 are selected to accommodate the water spike 152 without substantial additional space. For example, the width (or other dimension) of the recess 158 is preferably less than twice the width (or corresponding other dimension) of the water spike 152 and, in some configurations, is less than one and one-half times the width or less than one and one-quarter of the width.

Figure 7:
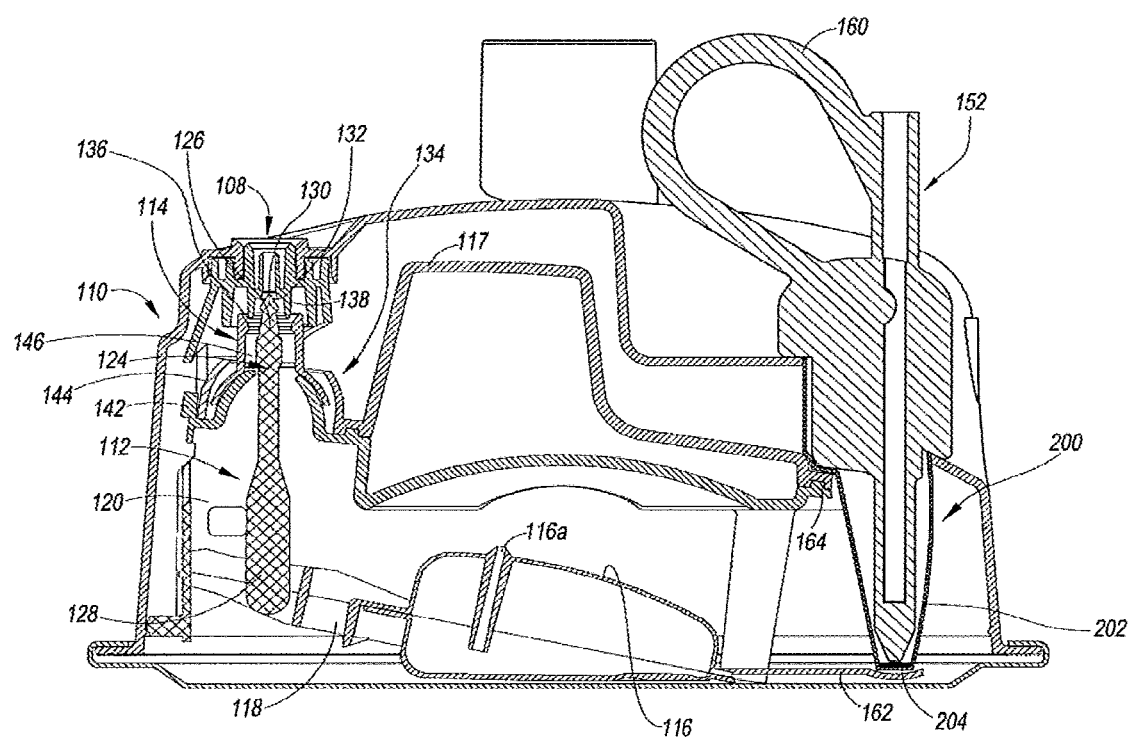
FIG. 7 is a sectional view of a humidification chamber having a float retention arrangement, such as the arrangement of FIGS. 1-4, wherein the access opening includes a cover or seal element.

In some embodiments, a cover or seal element 200 (FIG. 7) covers the access opening 154. In some embodiments, the seal element 200 comprises a flexible silicone membrane 202. The flexible silicone membrane 202 can additionally provide a protective sheath for the spike 152 to prevent contamination and damage to either or both of the spike 152 and float(s) 116, 117. The cover or seal 200 could be another type of stretchable membrane or other displaceable structure that stretches or moves to accommodate insertion of the spike 152 through the access opening 154. In some embodiments, the cover or seal 200 maintains a physical barrier around the spike 152 and between the spike 152 and the interior of the humidification chamber 100. The membrane 202 (or displaceable structure) could include a reinforcing portion or member 204 that inhibits or prevents the spike 152 from puncturing the membrane 202 (or displaceable structure). In some configurations, the cover or seal 200 could be a self-sealing membrane or valve (e.g., duckbill valve) that permits the spike 152 to pass through into the chamber 100 and that seals or substantially seals the access opening 154 when the spike 152 is withdrawn. A separate member (e.g., a plug) could be provided to block, cover, or seal the access opening once the spike is removed. The separate member could be coupled to the chamber cover, such as near the access opening with a leash, lanyard, receptacle or other suitable arrangement.

The access opening 154 can be positioned above a certain water level of the chamber 100 (e.g., a maximum or normal level) such that blocking, covering, or sealing of the access opening 154 is not necessary. Thus, in some configurations, the access opening 154 can be open to the atmosphere. However, in any arrangement regardless of the location of the access opening 154, a cover, block, or seal may be provided if desired.

Figure 5:
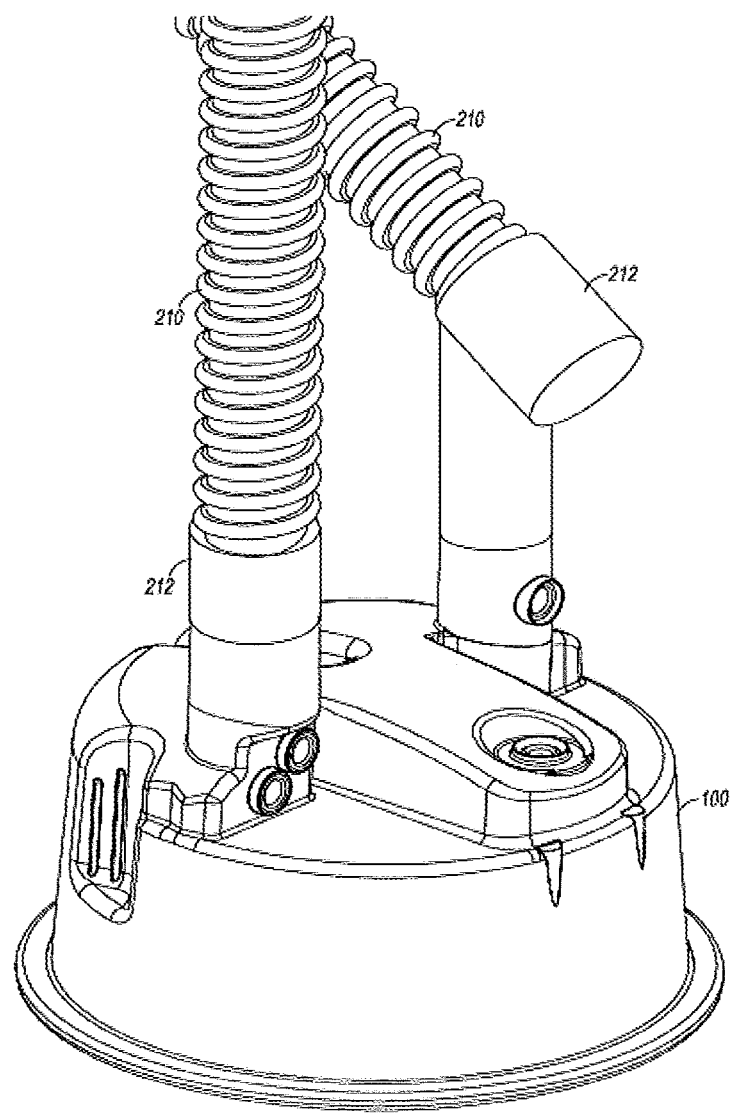
FIG. 5 is a perspective view of a humidification chamber having a float retention arrangement, such as the arrangement of FIGS. 1-4, illustrating that breathing tubes can be assembled with the float retention arrangement in use.

In some configurations, one or both of the inlet port 102 and the outlet port 104 of the chamber 100 are not obstructed by the float retention arrangement. Such an arrangement permits preassembly (such as during manufacture) or semi-permanent or permanent integration of breathing tubes 210, adapters 212 or other components to the inlet port 102 and/or outlet port 104, as illustrated in FIG. 5.

In some configurations, the present float retention arrangement intrinsically inhibits or prevents water from being introduced into the chamber 100 while the float retention arrangement is in place. One purpose of the water spike 152 is to retain the float(s) 116, 117 in the non-use position, but preferably the spike 152 is also the only path for water to pass to the inlet valve 108 through the supply tube or conduit 150 that extends between the inlet valve 108 and the water spike 152 (FIG. 1). Thus, in the illustrated arrangement there is no way for water to enter the chamber 100 through the inlet while the floats 116, 117 are retained in the non-use position and, thus, the valve arrangement 110 is held open. Advantageously, with such an arrangement, water cannot be accidentally introduced into the humidification chamber 100 via the normal pathway of the supply tube 150 while the valve arrangement 110 controlling the water inlet 108 is held open by a float retention arrangement. Therefore, accidental overfilling of the humidification chamber 100 can be avoided.

Figure 6:
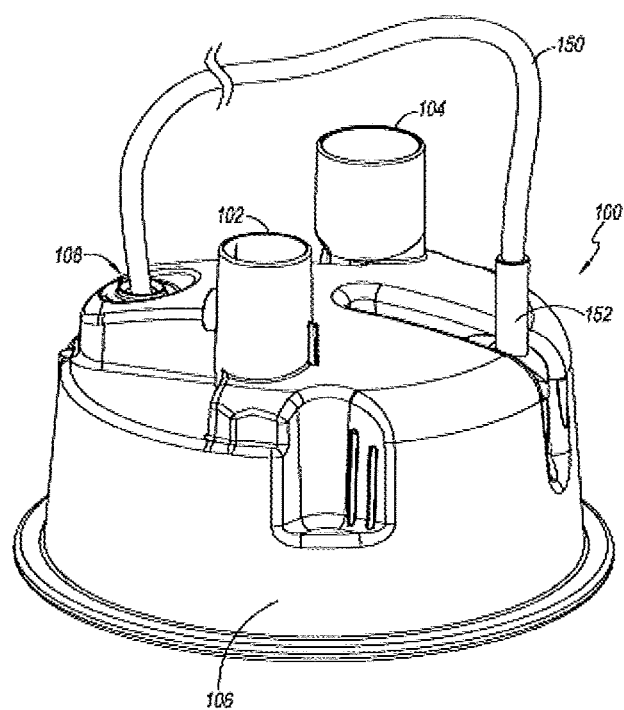
FIG. 6 is a perspective view of a humidification chamber having a float retention arrangement, such as the arrangement of FIGS. 1-4, wherein the water spike omits the finger loop.

The water spike 152 can have any suitable structure to cooperate with a suitable water supply (e.g., water bag) and function as a float retention device. For example, the water spike 152 can include a grip portion, such as a handle or finger loop 160, as shown in FIGS. 1-4. Alternatively, the water spike 152 can omit the handle or finger loop, as shown in the arrangement of FIG. 6. Such an arrangement can include a body of the water spike 152 that is sized and shaped or otherwise configured to facilitate gripping and removal of the water spike 152. The water spike 152 comprises a passage or conduit 174 for water to move from a tip 172 of the water spike 152 to the supply tube 150.

Figure 4:
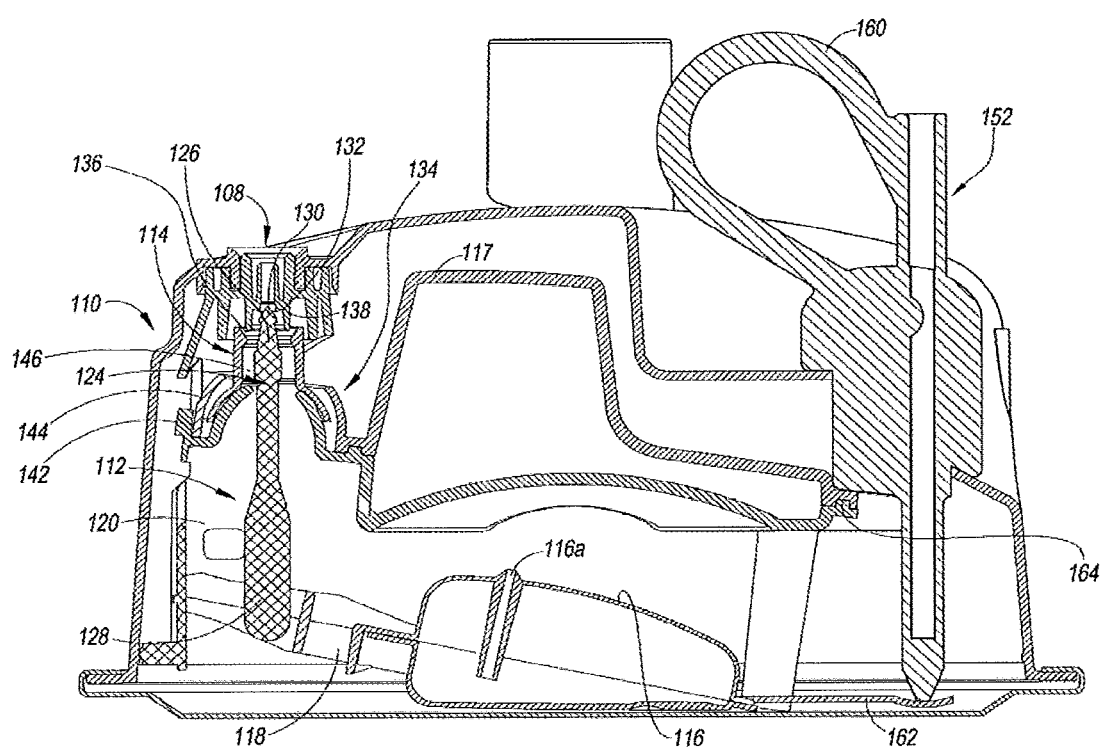
FIG. 4 is a sectional view of the humidification chamber of FIG. 1 illustrating a dual valve arrangement and interaction between the water spike, the cover of the chamber and the floats.

The water spike 152 (or other retention component) can engage the float(s) 116, 117 in any suitable manner. In some configurations, the tip 172 of the water spike 152 contacts one of the floats (e.g., the primary float). The water spike 152 can comprise a thin web portion 170 that extends through the access opening 154 and has a lower end portion that contacts one of the floats (e.g., the secondary float). FIG. 4 illustrates one example of possible water spike 152 contact positions with the floats 116, 117 (i.e., the retention locations). In some configurations, the water spike 152 contacts both floats 116, 117. In the illustrated arrangement, the water spike 152 contacts the front portion of each float 116, 117, preferably at a location forward of an axis of the gas inlet port 102 and/or outlet port 104, which can be forward of an entirety of the gas inlet port 102 and/or outlet port 104.

The primary float 116 can include a tab, arm 162 or other structure that extends away from (e.g., forwardly from) a main body of the float 116 and is contacted or otherwise engaged by the water spike 152. Similarly, the secondary float 117 can include a tab 164, arm or other structure that extends from (e.g., forwardly from) a main body of the float 117 that is contacted or otherwise engaged by the water spike 152. In the illustrated arrangement, the primary float 116 includes an elongate arm 162 and the secondary float 117 includes a relatively small tab 164; however, other suitable arrangements can be used, including the water spike 152 contacting a main body or buoyant portion of the floats 116, 117. In the illustrated arrangement, the water spike 152 retains one or both of the floats 116, 117 in a downward position e.g., fully downward corresponding to a fully open position of the valves 112, 114.

The water spike 152 can define surfaces 176, 178 that contact and rest upon the cover 156 with the water spike 152 in position to contact the floats 116, 117. The surfaces 176, 178 can be defined by a main body portion of the water spike 152. The surfaces 176, 178 can be positioned forward and rearward of the tip 172. The surfaces 176, 178 can be vertically offset from one another. One of the surfaces 176 can be angled relative to an axis of the water spike 152. One of the surfaces 178 can surround a portion of the web portion 170.

In the illustrated arrangement, the water spike 152 is located on a side of the chamber 100 opposite the water inlet 108. Preferably, the water inlet 108 is located on one side of a line extending through the axes of the gas inlet port 102 and outlet port 104 and the water spike 152 is located on an opposite side of the line when engaged with the chamber 100 as a float retention device. In such a position, the water spike 152 can be diametrically opposed to the water inlet 108. A line passing through both the water inlet 108 and the water spike 152 can be generally or substantially orthogonal to the line passing through the axes of the gas inlet port 102 and outlet port 104.

In at least some configurations, the inlet and outlet ports 102, 104 are not covered by the float retention device, thereby allowing factory pre-assembly or integration/permanent assembly of breathing tubes, adapters or other components to the humidification chamber. In at least some configurations, the float retention device intrinsically prevents the flow of water into the chamber while floats are held down. In at least some configurations, the float retention device reduces occurrence of impact damage and fatigue to the components of the float valve mechanism during transport and/or storage. In some configurations, the float retention device provides an inherent protective sheath for the water spike.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art, in this specification is not, and should not be taken as, an acknowledgement or any form of suggestion that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A circuit kit for a respiratory humidification system comprising:
    a humidifier chamber having a cover defining an interior space, a gas inlet port, a gas outlet port, a water inlet opening, a seal element and a float retention opening; and
    a component,
    wherein the seal element is configured to stretch or move to accommodate insertion of the component through the float retention opening such that the component is positionable to engage and retain at least one float in a non-use position.

2. The circuit kit of claim 1, wherein the humidifier chamber comprises the at least one float, wherein the at least one float comprises a first float and a second float.

3. The circuit kit of claim 2, wherein at least one of the first float and the second float is configured to operate an inlet valve that is configured to control a flow of water through the water inlet opening.

4. The circuit kit of claim 2, wherein the component comprises an adapter for connecting the humidifier chamber to a water source.

5. The circuit kit of claim 4, wherein the adapter is a water spike.

6. The circuit kit of claim 5, wherein the seal element maintains a physical barrier between the water spike and an interior of the humidifier chamber.

7. The circuit kit of claim 6, wherein the seal element comprises a membrane or a valve.

8. The circuit kit of claim 7, wherein the seal element is self-sealing.

9. The circuit kit of claim 6, wherein the seal element comprises a stretchable membrane configured to stretch to accommodate insertion of the water spike into the float retention opening.

10. The circuit kit of claim 9, wherein the stretchable membrane comprises a reinforced portion configured to prevent the water spike from puncturing the stretchable membrane.

11. The circuit kit of claim 5, wherein the seal element permits the water spike to pass through the float retention opening when inserted and substantially seals the float retention opening when the water spike is withdrawn.

12. The circuit kit of claim 11, wherein, when the water spike is positioned in the float retention opening, the water spike does not obstruct at least one of the gas inlet port and the gas outlet port such that breathing tubes, adapters or other components can be coupled to the at least one of the gas inlet port and the gas outlet port with the water spike positioned in the float retention opening.

13. The circuit kit of claim 5, wherein a portion of the water spike is positionable to engage at least one of the first float or the second float.

14. The circuit kit of claim 2, wherein at least one of the first float and the second float comprises buoyant structure configured to rise and fall with a water level within the humidifier chamber.

15. The circuit kit of claim 2, wherein at least one of the first float and the second float is coupled to humidification chamber.

16. The circuit kit of claim 15, wherein the first float is coupled to the humidification chamber with a coupling arm configured to support movement about an axis for rotation of the first float.

17. The circuit kit of claim 2, wherein the first float is coupled to the water inlet opening of the humidifier chamber.

18. The circuit kit of claim 2, wherein the first float is configured to operate an inlet valve that controls a flow of water through the water inlet opening in use.

19. The circuit kit of claim 1, wherein the component forms at least a portion of a water supply conduit for supplying water from a water source to the water inlet opening.

20. The circuit kit of claim 1, wherein the circuit kit comprises an inspiratory breathing tube and a gas supply tube, wherein the circuit kit is preassembled with the inspiratory breathing tube coupled to the gas outlet port and the gas supply tube to the gas inlet port.

* * * * *